US009155664B2

(12) United States Patent
Yamamoto (10) Patent No.: US 9,155,664 B2
(45) Date of Patent: Oct. 13, 2015

(54) CONVEYOR APPARATUS AND METHOD OF MANUFACTURING ABSORBENT ARTICLE

(75) Inventor: Hiroki Yamamoto, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 1067 days.

(21) Appl. No.: 12/743,983

(22) PCT Filed: Mar. 2, 2010

(86) PCT No.: PCT/JP2010/053744
§ 371 (c)(1),
(2), (4) Date: Oct. 17, 2012

(87) PCT Pub. No.: WO2010/101286
PCT Pub. Date: Sep. 10, 2010

(65) Prior Publication Data
US 2011/0049209 A1 Mar. 3, 2011

(30) Foreign Application Priority Data

Mar. 2, 2009 (JP) .............................. P2009-048445
Feb. 26, 2010 (JP) .............................. P2010-041940

(51) Int. Cl.
*B65H 20/06* (2006.01)
*B65H 20/10* (2006.01)
*A61F 13/15* (2006.01)

(52) U.S. Cl.
CPC .......... *A61F 13/15764* (2013.01); *B65H 20/06* (2013.01); *B65H 20/10* (2013.01); *B65H 2301/51214* (2013.01); *B65H 2801/57* (2013.01)

(58) Field of Classification Search
CPC .. A61F 13/15764; B65H 20/06; B65H 20/10; B65H 2301/51214; B65H 2801/57
See application file for complete search history.

(56) References Cited

U.S. PATENT DOCUMENTS

| 4,081,301 A | 3/1978 | Buell |
| 5,706,994 A | 1/1998 | Welch et al. |
| 2003/0010438 A1 | 1/2003 | Tharpe, Jr. et al. |

(Continued)

FOREIGN PATENT DOCUMENTS

| CA | 1206026 A1 | 6/1986 |
| EG | 2011081321 A1 | 8/2011 |
| EP | 1076131 A2 | 2/2001 |

(Continued)

OTHER PUBLICATIONS

Office Action issued Feb. 27, 2014, corresponds to Egyptian patent application No. 1470/2011.

(Continued)

*Primary Examiner* — William E Dondero
(74) *Attorney, Agent, or Firm* — Hauptman Ham, LLP (57) ABSTRACT

In a conveyor apparatus (100), a belt (110) is provided with a plurality of suction portions (111) penetrating the belt (110). The belt (110) includes lifting portions (113) each of which is provided between the suction portions (111) adjacent in a cross direction (CD) and lifts from edge portions (112) forming the suction portions (111). The plurality of suction portions (111) adjacent to each other across the lifting portions (113) communicate with each other, when a web (7) is sucked and held on the belt (110). The suction portions (111) located at endmost portions (110A) in the cross direction (CD) of the belt (110) communicate with the outside, when the web (7) is sucked and held on the belt (110).

9 Claims, 8 Drawing Sheets (56) References Cited

U.S. PATENT DOCUMENTS

2005/0103436 A1 5/2005 Otsubo et al.
2012/0018078 A1 1/2012 Ishikawa

FOREIGN PATENT DOCUMENTS

| EP | 1778915 A1 | 5/2007 |
|---|---|---|
| JP | 5726219 B2 | 6/1982 |
| JP | 6238997 Y2 | 10/1987 |
| JP | 06-205805 A | 7/1994 |
| JP | 06-245955 A | 9/1994 |
| JP | 8-28299 A | 1/1996 |
| JP | 08-258935 A | 10/1996 |
| JP | 08282899 A | 10/1996 |
| JP | 08-311791 A | 11/1996 |
| JP | 8300499 A | 11/1996 |
| JP | 8300500 A | 11/1996 |
| JP | 11-172591 A | 6/1999 |
| JP | 2001-151319 A | 6/2001 |
| JP | 2003145485 | 5/2003 |
| JP | 2004-073428 A | 3/2004 |
| JP | 2004-105696 A | 4/2004 |
| JP | 2004-115936 A | 4/2004 |
| WO | 9749554 A1 | 12/1997 |
| WO | 2008081239 A2 | 7/2008 |
| WO | 2010090107 A1 | 8/2010 |

OTHER PUBLICATIONS

Office Action issued Mar. 24, 2014, corresponds to Mexican patent application No. MX/A/2011/009140.
Office Action mailed Apr. 10, 2014, corresponds to Chinese patent application No. 201080010499.4.
Office Action issued Apr. 11, 2014, corresponds to Eurasian patent application No. 201101249.
Office Action issued Jul. 9, 2013 corresponds to Colombian patent application No. 11-128528.
Extended European Search Report issued Jul. 12, 2013 corresponds to EP Patent application No. 10748877.7.
Office Action issued Jun. 10, 2014, corresponds to European patent application No. 10748877.7.
Information Submission corresponding to JP 2010-041940, dated Nov. 20, 2012.
Office Action issued on Nov. 1, 2013, corresponds to Mexican patent application No. MX/a/2011/009140.
Office Action issued on Nov. 8, 2013, corresponds to Eurasian patent application No. 201101249.
Office Action mailed on Nov. 12, 2013, corresponds to Japanese patent application No. 2010-041940.
Office Action issued May 24, 2013 corresponding to EA patent application No. 201101249.
Office Action mailed Apr. 12, 2013 corresponds to Chilean patent application No. 2147-2011.
International Search Report and Written Opinion mailed May 25, 2010 corresponds to International application No. PCT/JP2010/053744.
Office Action mailed Aug. 28, 2013, corresponds to Chinese patent application No. 201080010499.4.
Office Action dated Oct. 10, 2014, corresponding to GCC patent application No. GC 2010-15376.
Office Action dated Jul. 21, 2015, corresponding to Australian patent application No. 2010221068.

CONVEYOR APPARATUS AND METHOD OF MANUFACTURING ABSORBENT ARTICLE

RELATED APPLICATIONS

The present application is national phase of PCT/JP2010/053744 filed Mar. 2, 2010, and claims priority from Japanese Application Number 2009-048445, filed Mar. 2, 2009 and Japanese Application Number 2010-041940, filed Feb. 26, 2010, the disclosures of which are hereby incorporated by reference herein in their entirety.

TECHNICAL FIELD

The present disclosure relates to a conveyor apparatus for conveying an air-permeable continuous web while sucking and holding the web on an endless belt rotating around multiple rollers, and to a method of manufacturing an absorbent article using such a conveyor apparatus.

BACKGROUND ART

A method of manufacturing an absorbent article such as a pants-type diaper, a sanitary napkin and a panty liner is implemented in an assembly line.

For instance, a continuous web including top sheets and bottom sheets to form absorbent articles is conveyed under tension in a conveyance direction of the web by a conveyor apparatus.

Then, component members such as a gather (stretchable member) and a waterproof film are placed on the web being conveyed under tension in the conveyance direction.

Meanwhile, the web might stretch or contract in a cross direction (so-called width direction of the web) perpendicular to the conveyance direction, where a stretchable component member, such as a gather or a waterproof film, is arranged.

Particularly, in a conveying method (so-called crosswise conveying method) in which a web is conveyed in a state where a pair of waistline portions to be fitted to the waistline of a wearer extend in the conveyance direction, the web under conveyance is often asymmetrical with respect to a center line in the width direction of the web, and contracts toward the center in the width direction of the web.

Under these circumstances, the inventor(s) is/are aware of a conveyor apparatus for suppressing potential stretch and contraction of the web in the width direction (see PTL 1, for example).

Such a conveyor apparatus includes an endless belt which rotates around multiple rollers, a drive mechanism configured to rotate the belt, and a suction mechanism. Multiple suction holes for sucking the web are formed in the belt. The suction mechanism is configured to suck and hold the web on the belt through the suction holes.

The inventors have discovered that the aforementioned conveyor has the following problem.

Specifically, the suction mechanism is configured to suck and hold the web on the belt by using the air passing through the web and the suction holes.

For this reason, a part of the web enters the suction holes. When a component member (for example, an absorber) is placed on the web while the part of the web enters the suction holes, an air pocket may be formed between the web and the component member, and consequently, may cause a manufacturing defect.

CITATION LIST

Patent Literature

PTL 1: Japanese Patent Application Publication No. 2003-145485 (pp. 2 to 4, FIGS. 1 and 2)

SUMMARY

It is desirable to provide a conveyor apparatus and a method of manufacturing an absorbent article which are capable of more reliably preventing a manufacturing defect due to an air pocket formed while suppressing potential stretch and contraction of the web in a width direction thereof when the web is conveyed on a belt.

To solve the above-described problem, the present invention has the following aspects. A first aspect of the present invention is summarized as a conveyor apparatus configured to convey a web while sucking and holding the web on an endless belt rotating around a plurality of rollers, the web including a continuum of air-permeable sheets, wherein the web is stretchable in a cross direction perpendicular to a conveyance direction of the web; the belt is provided with a plurality of suction portions penetrating the belt; the belt includes lifting portions each of which is provided between the suction portions adjacent in the cross direction and lifts from edge portions forming the suction portions; the plurality of suction portions adjacent to each other across the lifting portions communicate with each other, when the web is sucked and held on the belt; and the suction portions located at endmost portions in the cross direction of the belt communicate with the outside, when the web is sucked and held on the belt.

A second aspect of the present invention is summarized as a conveyor apparatus configured to convey a web while sucking and holding the web on an endless belt rotating around a plurality of rollers, the web including a continuum of air-permeable sheets, wherein the web is stretchable in a cross direction perpendicular to a conveyance direction of the web; a porous portion is provided on the belt and formed of a porous member; and side edges of the porous portion in the cross direction communicate with the outside.

A third aspect of the present invention is summarized as a method of manufacturing an absorbent article including an air-permeable sheet, the method comprising a step of conveying a web while sucking and holding the web on an endless belt provided to a conveyor, the web including a continuum of air-permeable sheets, wherein the web is stretchable in a cross direction perpendicular to a conveyance direction of the web; the belt is provided with a plurality of suction portions sucking the web and penetrating the belt; the belt includes lifting portions each of which is provided between the suction portions adjacent in the cross direction and lifts from edge portions forming the suction portions; the plurality of suction portions adjacent to each other across the lifting portions communicate with each other, when the web is sucked and held on the belt; and the suction portions located at endmost portions in the cross direction of the belt communicate with the outside, when the web is sucked and held on the belt.

BRIEF DESCRIPTION OF DRAWINGS

FIG. 5 (*a*) is an enlarged perspective view of a belt according to the first embodiment.

FIG. 5 (*b*) is a top view of the belt according to the first embodiment.

FIG. 5 (*c*) is a side view of the belt according to the first embodiment.

FIG. 6 (*a*) and FIG. 6 (*b*) are top views of a belt in various configurations according to a modified example 1.

DETAILED DESCRIPTION

Hereinafter, a conveyor and a method of manufacturing an absorbent article according to the present invention will be described with reference to the accompanying drawings. Specifically, a first embodiment, a second embodiment and other embodiments will be described.

Note that, in the following description of the drawings, same reference signs denote same elements and portions. In addition, it should be noted that the drawings are schematic and are not to scale unless otherwise specified. Therefore, specific dimensions and the like should be determined in consideration of the following description. Moreover, the drawings do not necessarily reflect the real-life dimensional relationships and ratios of components.

Therefore, specific dimensions and the like should be determined in consideration of the following description. Moreover, the drawings do not necessarily reflect the real-life dimensional relationships and ratios of components.

First, a structure of an absorbent article 1 according to one or more embodiments will be described with reference to FIG. 1 which is a partially cutaway perspective view of the absorbent article 1. In the particularly illustrated embodiment, the absorbent article 1 is a pants-type disposal diaper for adults.

Figure 1:
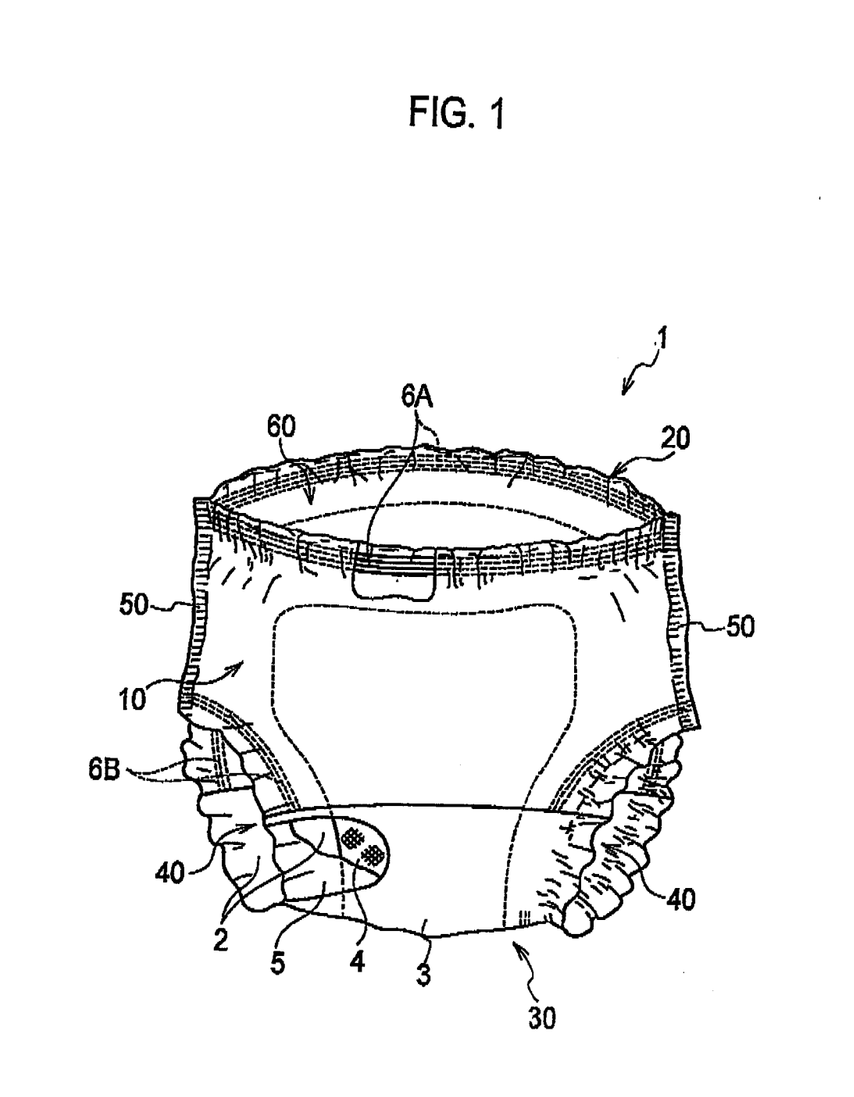
FIG. 1 is a partially cutaway perspective view of an absorbent article according to one or more embodiment of the present invention.

As shown in FIG. 1, the absorbent article 1 is formed mainly of a top sheet 2, a bottom sheet 3, an absorber 4 and a waterproof sheet 5.

The top sheet 2 is configured to come into contact with a skin of a person wearing the absorbent article 1 (hereinafter, referred to as "wearer"). As the top sheet 2, a liquid-permeable sheet, such as a non-woven fabric or a perforated plastic film, is used.

The back sheet 3 is provided outside the top sheet 2, in other words, the back sheet 3 is provided at the side farther from the wearer than top sheet 2. As the back sheet 3, a non-woven fabric or the like is used.

The absorber 4 is provided between the top sheet 2 and the back sheet 3, and is configured to absorb excretion of the wearer. As the absorber 4, a mixture of comminuted wood pulp and superabsorbent polymer particles, or the like, is used.

The waterproof sheet 5 is provided between the back sheet 3 and the absorber 4, and does not allow excretion of the wearer to permeate therethrough. The waterproof sheet 5 is made of a liquid-impermeable sheet.

The absorbent article 1 as described above is formed by combining: a front waistline portion 10 to be fitted to the front waistline of the wearer; a back waistline portion 20 to be fitted to the back waistline of the wearer; and the crotch portion 30 to be fitted to the crotch of the wearer.

Note that, leg-surrounding openings 40 are formed respectively at sides of the crotch portion 30, and the legs of the wearer are to be inserted through the leg-surrounding openings 40.

The front waistline portion 10 and the back waistline portion 20 are united by joint portions 50, and thus form a waistline opening 60 to be fit around the body of the wearer.

A waist gather 6A made of rubber strands or the like having stretchability is provided in the peripheral edges of the front waistline portion 10 and the back waistline portion 20.

For example, the front waistline portion 10 and the back waistline portion 20 may be provided with the waist gather 6A to be thus stretchable in a cross direction crossing a front-to-back direction extending from the front waistline portion 10 to the back waistline portion 20, or may themselves be formed of sheets having stretchability to be thus stretchable in the cross direction.

The crotch portion 30 is provided between the front waistline portion 10 and the back waistline portion 20.

Leg gathers 6B each made of rubber strands or the like having stretchability are provided respectively at the sides of the crotch portion 30.

For example, the crotch portion 30 may be provided with the leg gathers 6B to be thus stretchable in the front-to-back direction of the absorbent article 1, or may itself be formed of a sheet having stretchability to be thus stretchable in the front-to-back direction of the absorbent article 1.

Next, a method of manufacturing the absorbent article 1 according to one or more embodiments will be described with reference to FIG. 2 which is an explanatory view for explaining a relevant part of the method of manufacturing the absorbent article.

Figure 2:
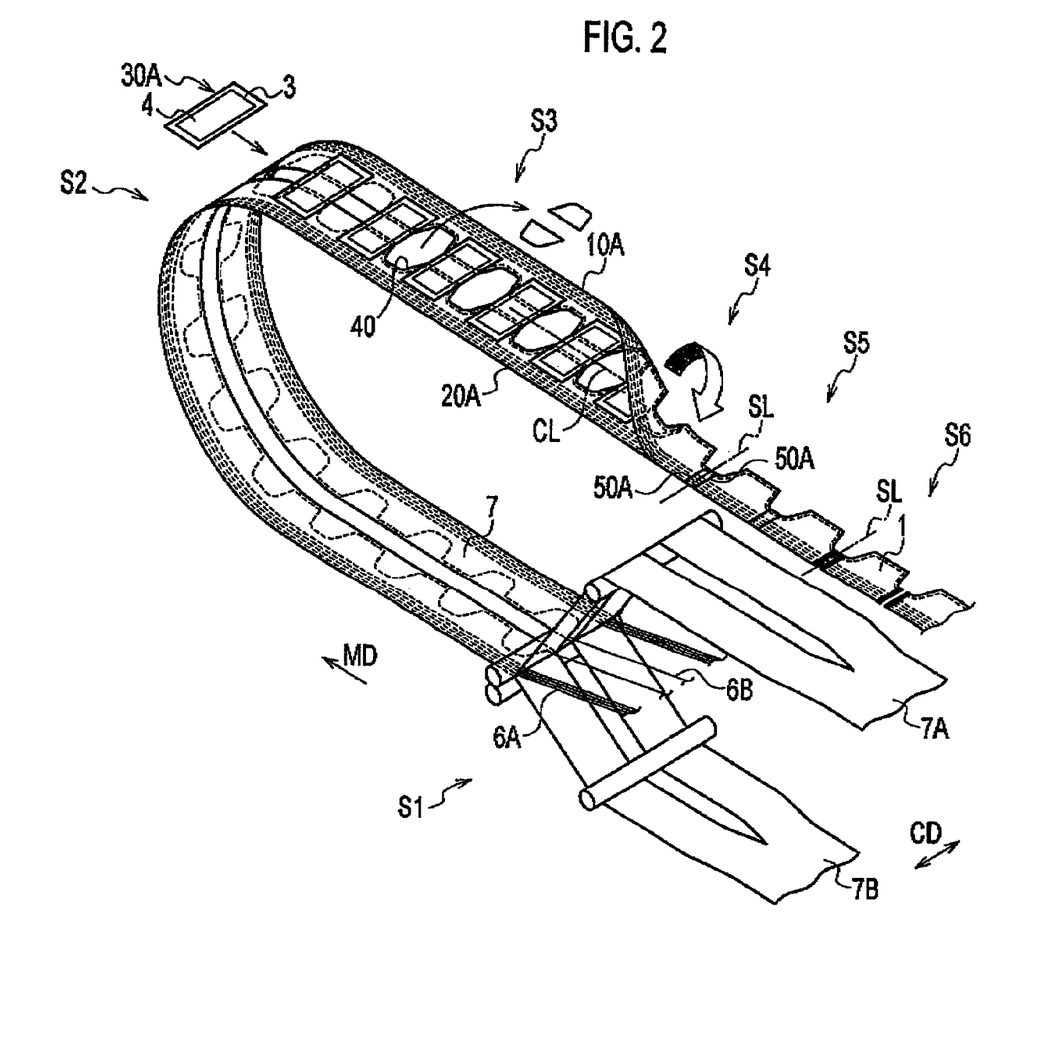
FIG. 2 is a diagram for explaining a relevant part of a method of manufacturing an absorbent article according to one or more embodiment of the present invention.

As shown in FIG. 2, the method of manufacturing the absorbent article 1 includes at least a waistline forming step S1, an absorber transferring step S2, a leg-surrounding opening forming step S3, a folding step S4, a joining step S5, and a cutting step S6.

In the waistline forming step S1, a web 7 is formed by disposing gathers (the waist gather 6A and/or the leg gathers 6B) between a web 7A and a web 7B. The web 7 is to be processed into the front waistline portion 10 and the back waistline portion 20.

Note that, the web 7 (the webs 7A and 7B) being conveyed is stretchable in a cross direction. CD (a width direction) orthogonal to a conveyance direction MD (Machine Direction) of the web 7.

In addition, the web 7 is asymmetrical with respect to a center line CL that bisects a width in the cross direction CD of the web 7 and extends in the conveyance direction MD of the web 7.

In the absorber transferring step S2, a crotch portion member 30A to be processed into the crotch portion 30 is transferred onto the web 7, specifically, between the front waistline portion 10 and the back waistline portion 20, after the waistline forming step S1. Note that, the crotch portion member 30A is formed of the back sheet 3 and the absorber 4.

In the leg-surrounding opening forming step S3, the leg-surrounding openings 40 (so-called leg holes) are formed by cutting the web 7 (the webs 7A and 7B) after the absorber transferring step S2.

Note that, the leg-surrounding openings 40 are not necessarily formed by cutting only the web 7 (the webs 7A and 7B), but may alternatively be formed by cutting the back sheet 3 forming the crotch portion member 30A together with the web 7A and the web 7B.

Here, the absorber transferring step S2 and the leg-surrounding forming step S3 may be performed in the reverse order.

In the folding step S4, the web 7 is folded in half along a folding line extending in the conveyance direction MD of the web 7, by bringing a side edge 10A of the front waistline portion 10 in the web 7 toward a side edge 20A of the back waistline portion 20 in the web 7, after the leg-surrounding opening forming step S3.

Note that, in the particularly illustrated embodiment, the folding line is the same as the center line CL. Moreover, the folding line does not necessarily coincide with the center line CL, and may be offset from the center line CL toward the side edge 10A or toward the side edge 20A.

In the joining step S5, the folded parts of the web 7 are joined at joint regions 50A to be processed into the joint portions 50 of the absorbent article 1 by an ultrasonic treatment or a heat treatment, after the folding step S4.

Note that the joint regions 50A respectively indicate regions at both sides of an imaginary line SL in the conveyance direction MD. The imaginary line SL indicates a cutting line extending in the cross direction CD.

In the cutting step S6, the web 7 in which the joint regions 50A have been joined is cut along the imaginary line SL after the joining step S5. As a result, the absorbent article 1 is manufactured.

Note that the web 7 is conveyed by conveyor apparatuses 100 to be described later in the respective steps (S1 to S6). The web 7 is stretchable in at least the cross direction CD of the web 7 (so-called a width direction of the web 7).

Next, a configuration of the conveyor apparatus 100 used in the aforementioned steps (S1 to S6) will be explained with reference to the drawings.

First Embodiment

Figure 3:
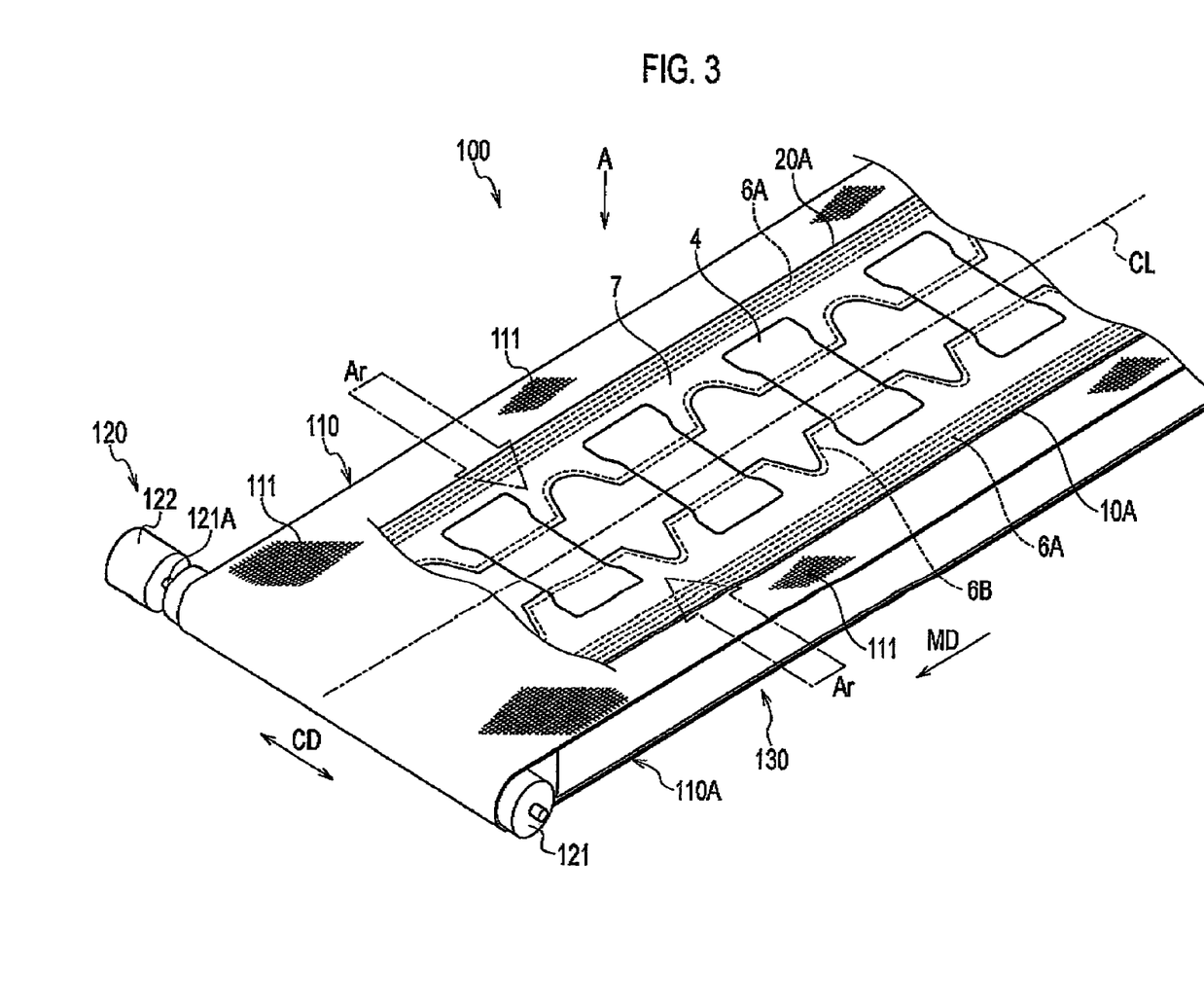
FIG. 3 is a perspective view of a part of a conveyor apparatus according to a first embodiment.
Figure 4:
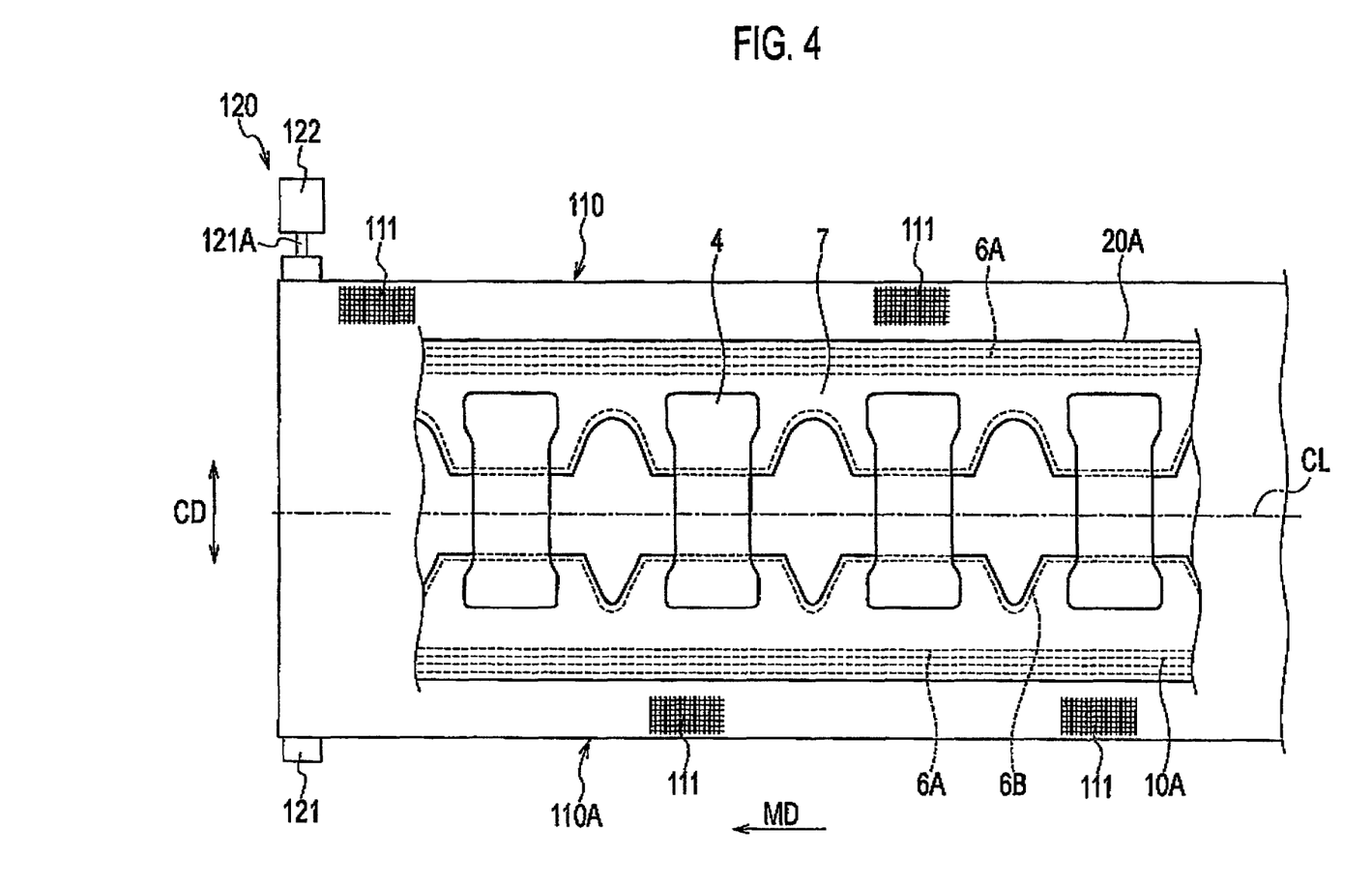
FIG. 4 is a top view of the conveyor apparatus (as seen in the direction of an arrow A of FIG. 3) according to the first embodiment.

FIG. 3 is a perspective view of a part of a conveyor apparatuses 100 according to the first embodiment. FIG. 4 is a top view of the conveyor apparatuses 100 according to the first embodiment (as seen in the direction of an arrow A of FIG. 3).

Note that one or more of the conveyor apparatuses 100 can be used in any one and/or between any pair of the steps (S1 to S6), and thus a description will be given, as an example, for the conveyor apparatus 100 which is used between the leg-surrounding opening forming step S3 and the folding step S4.

As shown in FIGS. 3 and 4, the conveyor apparatus 100 conveys the web 7 while sucking and holding the web 7 on a belt 110. Specifically, the conveyor apparatus 100 includes the belt 110, a drive mechanism 120 and a suction mechanism 130.

The belt 110 is an endless belt rotating around multiple rollers of the drive mechanism 120 (for example, a drive roller 121 and unillustrated rollers). A configuration of the belt 110 will be described later.

The drive mechanism 120 is configured to rotate the belt 110. The drive mechanism 120 includes the above-mentioned multiple rollers and a drive unit 122.

At least one drive roller 121 among the multiple rollers is rotated about a shaft 121A by the drive unit 122. The drive unit 122 has a motor configured to rotate the drive roller 121 via the shaft 121A, and the like.

The suction mechanism 130 is configured to suck the air through suction portions 111 to be described later. In other words, the suction mechanism 130 is configured to suck and hold a part of the web 7, which is located on the belt 110, onto the belt 110.

Figure 5:
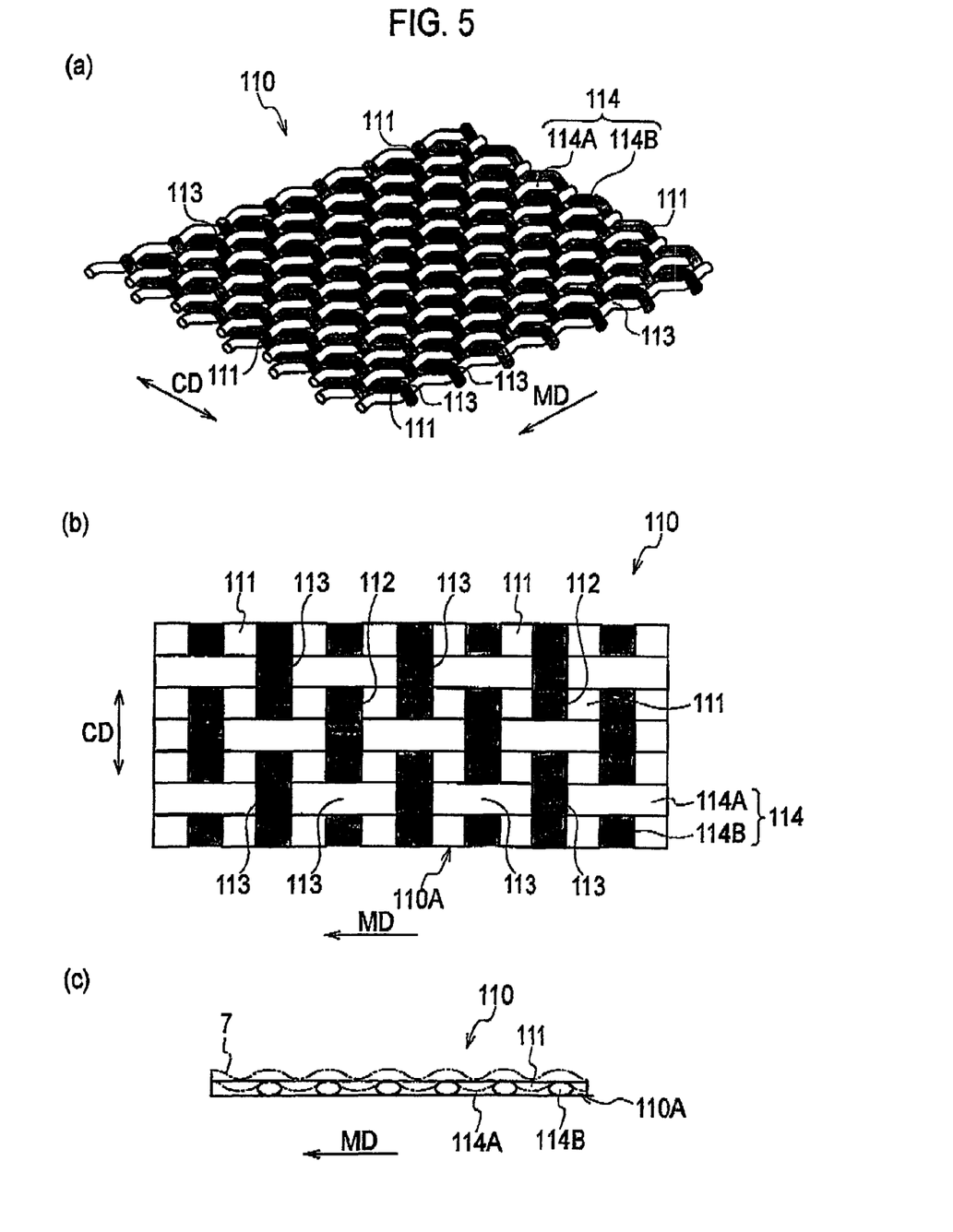

Next, a configuration of the belt 110 described above will be explained with reference to FIGS. 3 to 5. Note that FIG. 5 (*a*) is an enlarged perspective view of the belt 110 according to the first embodiment. FIG. 5 (*b*) is a top view of the belt 110 according to the first embodiment. FIG. 5 (*c*) is a side view of the belt 110 according to the first embodiment.

As shown in FIGS. 4 to 5(*c*), the belt 110 is provided with multiple suction portions (openings) 111 penetrating the belt 110. The belt 110 further includes lifting portions 113 each being raised from edge portions 112 of the suction portions 111.

A lifting portion 113 is provided between each pair of adjacent suction portions 111 in the cross direction CD of the web 7.

Additionally or alternatively, a lifting portion 113 is provided between each pair of adjacent suction portions 111 in the conveyance direction MD of the web 7.

In a plan view of the belt 110, the total area of the lifting portions 113 is smaller than the total area of the suction portions 111.

The suction portions 111 and lifting portions 113 are formed by weaving wires 114 in crossing directions. Specifically, each lifting portion 113 is defined by one wire 114, that extends in one of the crossing directions, going over another wire 114, that extends in the other one of the crossing directions.

The belt 110 is preferably provided in some embodiments with the wires 114 having 10 to 20 meshes per inch. In addition, the wires 114 are preferably made in some embodiments of polyethylene terephthalate, polyimide, polypropylene, polyvinylidene fluoride, or the like.

The diameter of the weaving wires 114 can be set between 0.02 mm and 1.9 mm. Suction pressure has to be set in a level that accomplishes holding of the web 7 and no damages occur on the web 7. Since the belt 110 is formed by the wires 114, the Suction pressure can be selected from the wider range in comparison with the conventional one.

The wires 114 include first wires 114A and second wires 114B. The first wires 114A extend in the conveyance direction MD of the web 7. The second wires 114B cross the first wires 114A and extend in the cross direction CD of the web 7.

Specifically, each of the first wires 114A is woven alternately over every second one then under the next one of the second wires 114B.

Meanwhile, each of the second wires 114B is woven alternately over every second one then under the next one of the first wires 114A.

In this structure, the suction portions 111 and the lifting portions 113 are adjacent to each other in both the conveyance direction MD and the cross direction CD of the web 7.

As described above, while the web 7 is sucked and held on the belt 110, the multiple suction portions 111 adjacent to each other across the lifting portions 113 communicate with each other.

In addition, while the web 7 is sucked and held on the belt 110, the suction portions 111 located in endmost portions 110A of the belt 110 in the cross direction CD communicate with the outside.

In the first embodiment 1 described above, the lifting portions 113 are each provided between each pair of the suction portions 111 adjacent in the cross direction CD of the web 7.

With this structure, the web 7 stretchable in the cross direction CD of the web 7 is likely to be gripped by the lifting portions 113.

Accordingly, a resistance generated between the web 7 and the lifting portions 113 can inhibit the web 7 from stretching or contracting in the cross direction CD of the web 7 (so-called width direction), particularly, from contracting toward the center in the width direction.

In addition, while the web 7 is sucked and held on the belt 110, the multiple suction portions 111 adjacent to each other across the lifting portions 113 communicate with each other.

With this structure, the air is less likely to remain at one location (one suction hole) than in the case where the web 7 is sucked and held on the belt 110 merely through the suction holes. This prevents a part of the web 7 from entering the suction portions 111.

Moreover, when the web 7 is sucked and held on the belt 110, the suction portions 111 located in the endmost portions 110A of the belt 110 in the width direction communicate with the outside.

With this structure, the air always enters through the suction portions 111 located in the endmost portions 110A in the width direction (indicate by arrow Ar in FIG. 3), and thus there exists the air between the suction portions 111 and the web 7.

Accordingly, a part of the web 7 located above the suction portions 111 floats and thus the part of the web 7 is reliably prevented from entering the suction portions 111.

As described above, in the first embodiment, it is possible to inhibit a component member (for example, the absorber 4) from being placed on the web 7 with a part of the web 7 entering the suction portion 111.

Therefore, a manufacturing defect due to an air pocket generated between the web 7 and the component member can be prevented more reliably.

In the first embodiment, the lifting portions 113 are each provided between each pair of the suction portions 111 adjacent in the conveyance direction MD of the web 7.

This increases the area in which the web 7 is gripped by the lifting portions 113. Accordingly, the resistance generated between the web 7 and the lifting portions 113 can more reliably inhibit the web 7 from stretching or contracting in the width direction, particularly, from contracting toward the center in the width direction.

In the first embodiment, the belt 110 has been disclosed as having the wires 114 of 10 to 20 meshes per inch.

When the number of meshes of the wires 114 per inch is less than 10, the resistance generated between the web 7 and the lifting portions 113 may be insufficient to inhibit the web 7 from stretching or contracting in the width direction.

By contrast, when the number of meshes of the wires 114 per inch is more than 20, the area of the suction portions 111 is too small, and thus a suction force generated by the suction mechanism 130 via the suction portions 111 might be insufficient to hold the web 7 on the belt 110.

In the first embodiment, the wires 114 has been disclosed to be made of polyethylene terephthalate, polyamide, polypropylene, polyvinylidene fluoride, or the like. This enhances the durability of the belt 110 and increases the service life of the belt 110.

In the first embodiment, the total area of the lifting portions 113 is smaller than the total area of the suction portions 111 in the plan view of the belt 110.

This increases the suction force sucking and holding the web 7 on the belt 110, in comparison with a case where the total area of the lifting portions 113 is larger than the total area of the suction portions 111.

Accordingly, it is possible to more reliably prevent the web 7 from stretching or contracting in the width direction, particularly, from contracting toward the center in the width direction.

Modified Examples

The belt 110 according to the first embodiment described above may be modified as follows. Note that the description will be provided mainly for the differences from the foregoing description, with the same or reference signs denoting the same or similar elements.

Modified Example 1

First, a configuration of a belt 210A according to a modified example 1 is explained with reference to FIG. 6 (*a*) and FIG. 6 (*b*) which are top views of a belt 210A in various configurations according to the modified example 1.

In the first embodiment, each second wire 114B is woven alternately over every second one then under the next one of the first wires 114A.

Figure 6:
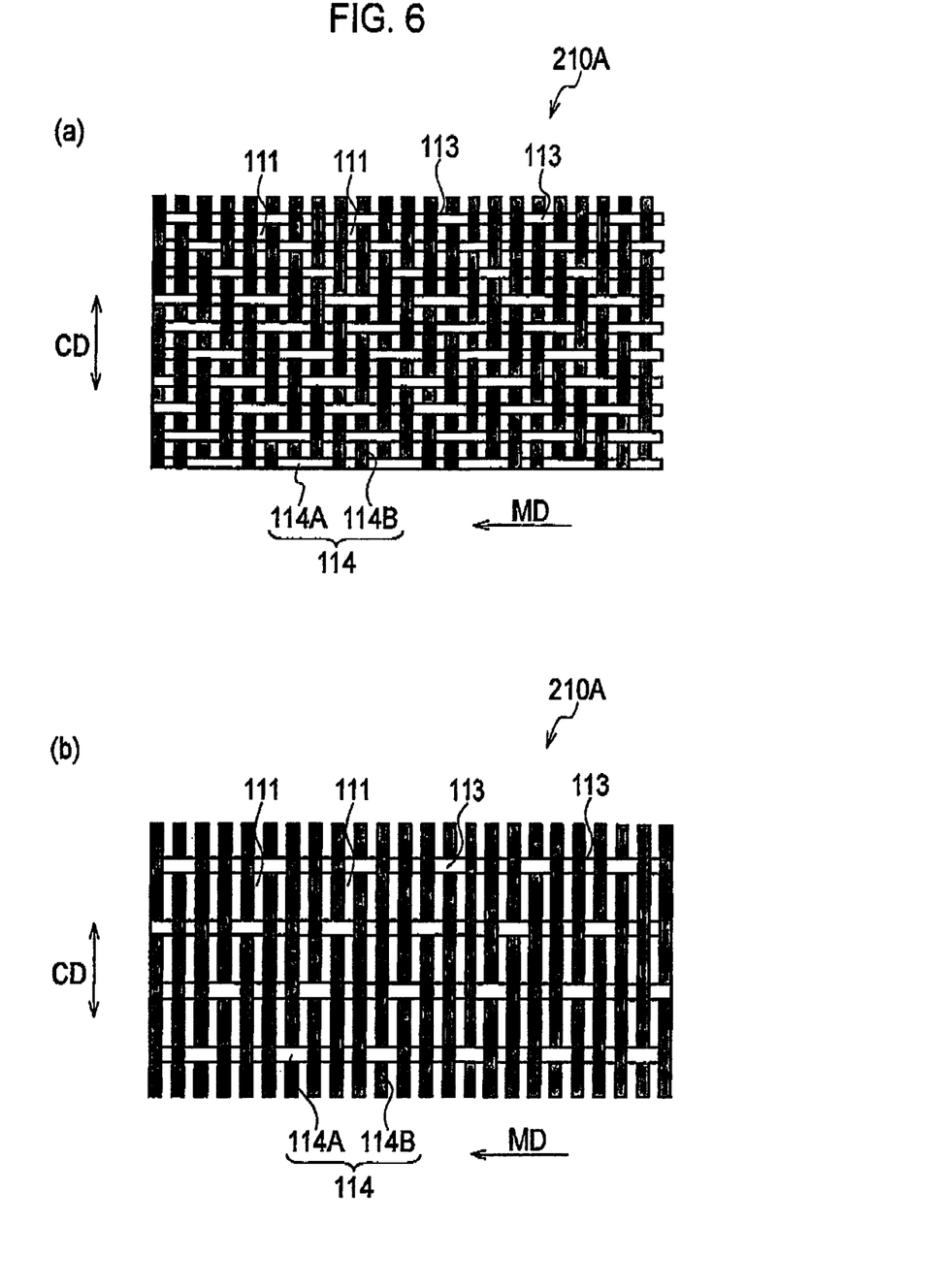

By contrast, in the modified example 1, each second wire 114B is woven over every two then under the next two of the first wires 114A, as shown in FIG. 6 (*a*).

Alternatively, each second wire 114B may be woven under every three then under the next three of the first wires 114A, as shown in FIG. 6 (*b*).

Generally speaking, each first wire 114A may be woven over N of the second wires 114B and then under the next M of the second wires 114B, where M and N are integers greater than 1 and M is the same of different from N. Similarly, each second wire 114B may be woven over P of the first wires 114A and then under the next Q of the first wires 114A, where P and Q are integers greater than 1, and M, N, P, Q can be mutually the same or different.

Modified Example 2

Next, a configuration of a belt 210B according to a modified example 2 will be explained with reference to FIG. 7 which is a top view of the belt 210B.

In the first embodiment, the total area of the lifting portions 113 is smaller than the total area of the suction portions 111 in the plan view of the belt 110.

Figure 7:
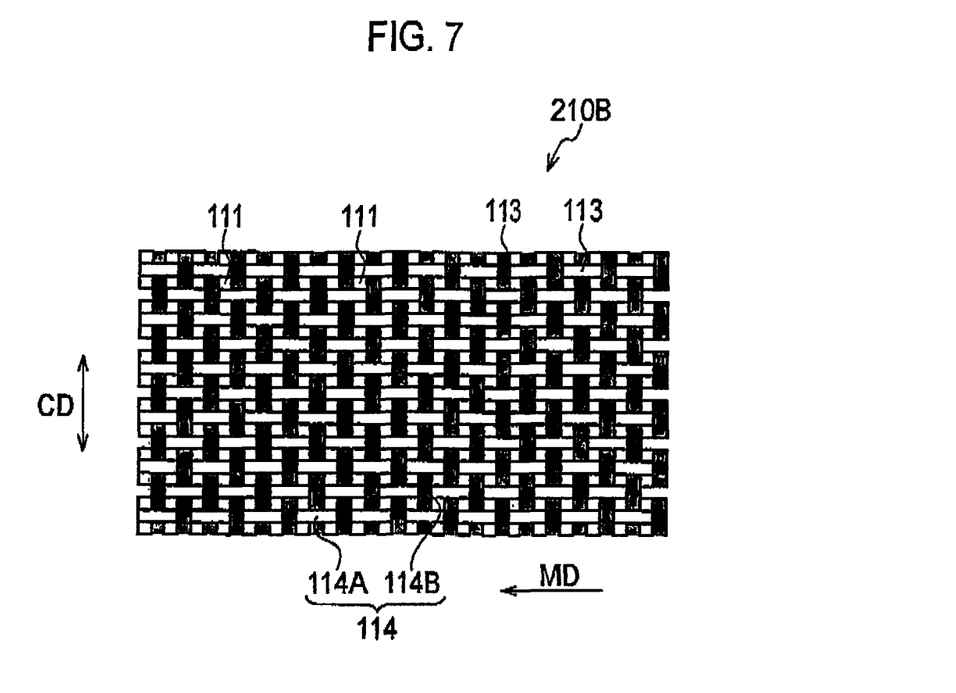
FIG. 7 is a top view of a belt according to a modified example 2.

By contrast, in the modified example 2, the total area of the lifting portions 113 is larger than the total area of the suction portions 111 in a plan view of the belt 210B, as shown in FIG. 7.

Note that the total area of the lifting portions 113 does not necessarily have to be larger than the total area of the suction portions 111, but may be the same as the total area of the suction portions 111.

Modified Example 3

Next, a configuration of the belt 210C according to a modified example 3 will be explained with reference to FIG. 8 which is a top view of the belt 210C.

In the first embodiment, the lifting portions 113 are each provided between each pair of the suction portions 111 adjacent in both the conveyance direction MD and the cross direction CD of the web 7.

In other words, the wires 114 arranged in crossing directions are woven with each other in both the conveyance direction MD and the cross direction CD of the web 7.

Figure 8:
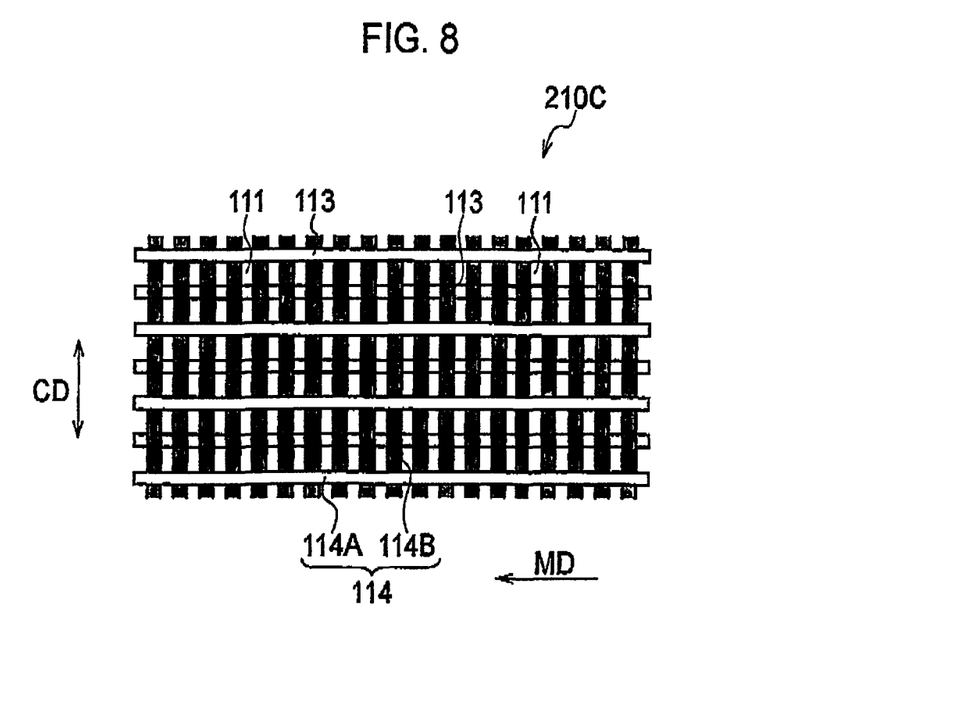
FIG. 8 is a top view of a belt according to a modified example 3.

By contrast, in the modified example 3, the lifting portions 113 are each provided between each pair of the suction portions 111 adjacent in the cross direction CD of the web 7 only, as shown in FIG. 8.

In other words, the wires 114 are woven with each other only in the cross direction CD of the web 7. Similarly, the wires 114 may be woven with each other only in the conveyance direction MD of the web 7.

Second Embodiment

Hereinafter, a configuration of a conveyor 100A according to a second embodiment will be explained with reference to FIG. 9 which is a perspective view of a part of the conveyor apparatus 100A. Note that the description will be provided mainly for the differences from the foregoing description, with the same or similar reference signs denoting the same or similar elements.

Note that the conveyor apparatus 100 according to the first embodiment described above includes the belt 110, the drive mechanism 120 and the suction mechanism 130.

On the other hand, the conveyor apparatus 100A according to the second embodiment includes a porous portion 150 in addition to the configuration of the conveyor apparatus 100 according to the first embodiment.

Figure 9:
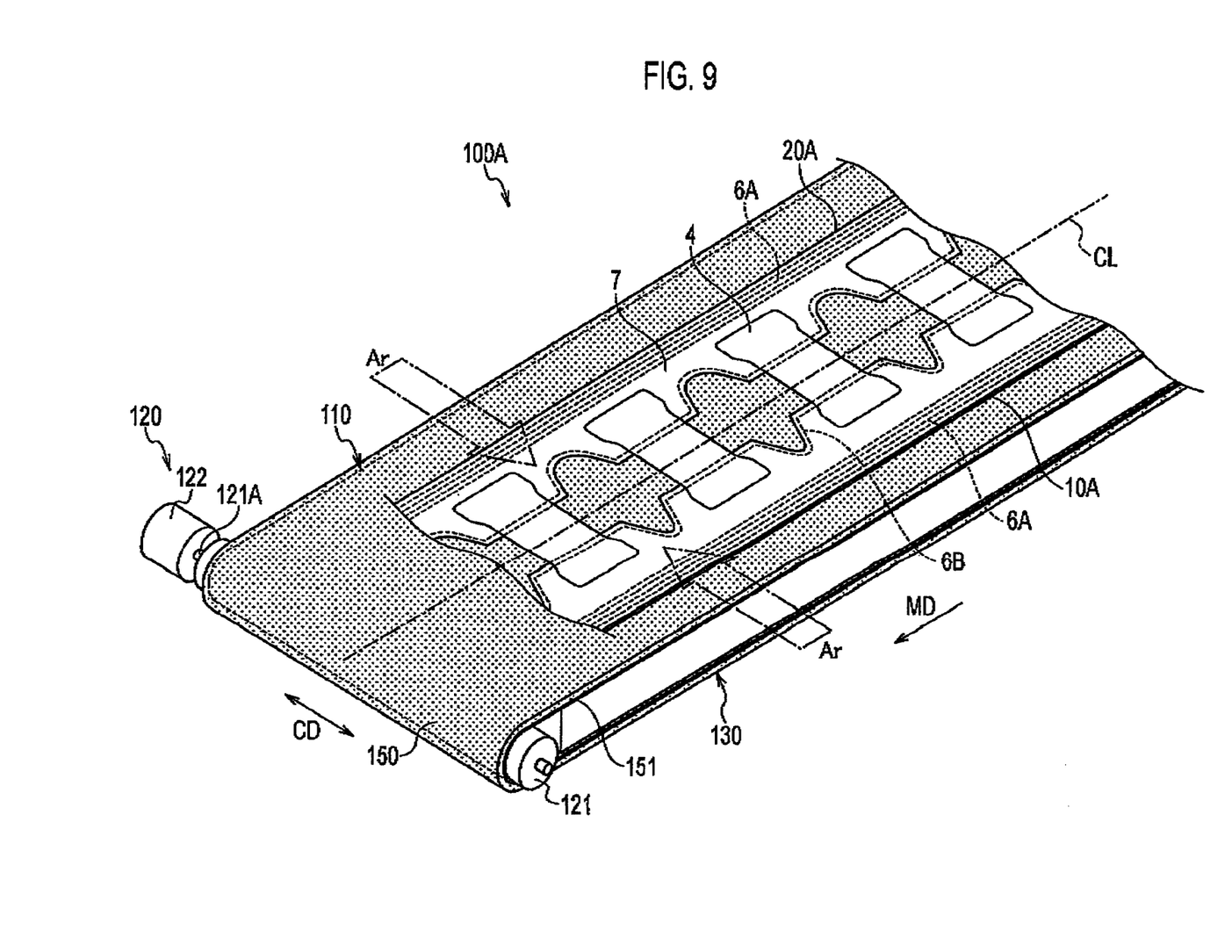
FIG. 9 is a perspective view of a part of a conveyor apparatus according to a second embodiment.

Specifically, as shown in FIG. 9, the porous portion 150 is formed of a porous member (for example, sponge). The porous portion 150 is provided on the belt 110. The porous portion, in some embodiments, has a 3-D network of communicating pores.

The porous member having void ratio that results in certain suction pressure can be used. The certain suction pressure accomplishes holding of the web 7 and no damages occur on the web 7.

This means that the web 7 is sucked and held on the belt 110 with the porous portion 150 interposed therebetween. Side edges 151 of the porous portion 150 in the width direction have pores that are construed to communicate with the outside and also construed to communicate with the other pores of the porous portion.

Here, the belt 110 according to the second embodiment may have the configuration described in the aforementioned the first embodiment, or may have the configuration in which suction holes are formed as described in the background art.

As disclosed above, in the second, embodiment, the side edges 151 of the porous portion 150 have pores that communicate with the outside and also communicate with the other pores of the porous portion.

Thereby, it is unlikely that a part of the web 7 might enter the pores of the porous portion 150, like the advantageous effects of the first embodiment described above.

Therefore, it is possible to more reliably prevent a manufacturing defect due to an air pocket generated between the web 7 and a component member to be placed on the web 7 while the web 7 is being held by the conveyor apparatus 100A according to the second embodiment.

Further Embodiments

As described above, the details of several embodiments of the present invention have been exemplarily disclosed. It should not be understood that the description and drawings which constitute part of this disclosure limit the present invention. Based on this disclosure, those skilled in the art may easily come up with various alternative embodiments, examples and operation techniques.

For example, the following additional embodiments can be envisaged. Specifically, the absorbent article 1 has been described as including, in combination, the front waistline portion 10, the back waistline portion 20 and the crotch portion 30.

The absorbent article 1 is not limited to this configuration, but may be formed entirely as a single unit. In this case, needless to say, a different method of manufacturing an absorbent article is employed.

Additionally, the description has been provided for the conveyor apparatus 100 used in the manufacturing of a pants-type disposal diaper.

However, the conveyor 100 is not limited to such use. For example, the conveyor apparatus 100 may be used to manufacture any wearing article, such as open-type disposal diapers, sanitary napkins and panty liners.

In other words, the conveyor apparatus 100 may be used at least for the conveyance of any web that is stretchable in the cross direction CD, not necessarily for manufacturing of the absorbent article 1.

According to one or more aspect(s) of the present invention, there can be provided a conveyor apparatus and a method of manufacturing an absorbent article which are capable of more reliably preventing a manufacturing defect due to an air pocket, while suppressing potential stretch and contraction of the web in a width direction thereof when the web is conveyed on a belt.

As described above, the present invention naturally includes various embodiments which are not described herein. Accordingly, the technical scope of the present invention should be determined only by the elements of the invention in the scope of claims regarded as appropriate based on the description.

The entire content of Japanese Patent Applications 2009-048445 (filed on Mar. 2, 2009) and 2010-041940 (filed on Feb. 26, 2010) are incorporated herein by reference.

INDUSTRIAL APPLICABILITY

Therefore, according to the present invention, since it is possible to provide a conveyor apparatus and a method of manufacturing an absorbent article which are capable of more reliably preventing a manufacturing defect due to an air pocket while suppressing the stretch and contraction of the web in a width direction thereof when the web is conveyed on a belt, it is useful in manufacturing technology for absorbent articles.

REFERENCE SIGNS LIST 1 absorbent article
2 top surface sheet
3 bottom surface sheet
4 absorber
5 waterproof sheet
6 leg gather
6A waist gather
6B leg gather
7, 7A, 7B web
10 front waistline portion
10A first side edge
20 back waistline portion
20A second side edge
30 crotch portion
40 leg-surrounding openings
50 joint portion
50A joint region 60 waist openings
100, 100A conveyor
110 (210A to 210C) belt
110A endmost portion
111 suction portion
112 edge portion
113 lifting portion
114 cord
114A first cord
114B second cord
120 drive mechanism
121 drive roller
121A shaft core
122 drive unit
130 suction mechanism
150 porous portion
151 side edge

The invention claimed is:

1. A combination of an air-permeable continuous web, wherein the web is stretchable in a cross direction perpendicular to a conveyance direction of the web and a conveyor apparatus for conveying the web, said conveyor apparatus comprising:
   an endless belt rotatably supported by a plurality of rollers and having a plurality of suction portions penetrating the belt; and
   a suction mechanism for sucking and holding, via the suction portions, the web on the belt while the web is being conveyed;
   wherein
   the belt further includes lifting portions each of which is provided between the suction portions adjacent in the cross direction and is raised from edge portions of the suction portions;
   the plurality of suction portions adjacent to each other across the lifting portions communicate with each other, when the web is sucked and held on the belt;
   the suction portions located at endmost portions in the cross direction of the belt communicate with the outside, when the web is sucked and held on the belt;
   the web includes:
      a front waistline portion, a back waistline portion, and a crotch portion arranged between the front waistline portion and the back waistline portion in the cross direction;
      waist gathers which are disposed at a peripheral edge of the front waistline portion and a peripheral edge of the back waistline portion; and
      leg gathers which are disposed at both sides of the crotch portion; and
   the web is asymmetrical with respect to a center line, the center line bisecting a width of the web in the cross direction and extending in the conveyance direction.

2. The combination according to claim 1, wherein the lifting portions are each further provided between the suction portions adjacent in the conveyance direction.

3. The combination according to claim 1, wherein the suction portions and the lifting portions are defined by wires crossing each other,
   the wires include:
      a plurality of first wires extending in the conveyance direction; and
      a plurality of second wires crossing the plurality of first wires and extending in the cross direction,
   each first wire among the plurality of first wires is completely arranged above or below the plurality of second wires, and
   each second wire among the plurality of second wires is arranged above some first wires and below other first wires among the plurality of first wires.

4. The combination according to claim 1, wherein the belt is provided with the wires having 10 to 20 meshes per inch.

5. The combination according to claim 3, wherein each second wire among the plurality of second wires passes alternately over one first wire and under one adjacent first wire among the plurality of first wires.

6. The combination according to claim 1, wherein the suction portions and the lifting portions are defined by wires woven with each other,
   the wires include:
      a plurality of first wires extending in the conveyance direction; and
      a plurality of second wires crossing the plurality of first wires and extending in the cross direction,
   each first wire among the plurality of first wires passes alternately over two second wires and under two adjacent second wires among the plurality of second wires, and
   each second wire among the plurality of second wires passes alternately over two first wires and under two adjacent first wires among the plurality of first wires.

7. The combination according to claim 1, wherein the total area of the lifting portions is smaller than the total area of the suction portions.

8. The combination according to claim 1, wherein the suction portions and the lifting portions are defined by wires woven with each other,
   the wires include:
      a plurality of first wires extending in the conveyance direction; and
      a plurality of second wires crossing the plurality of first wires and extending in the cross direction,
   each first wire among the plurality of first wires passes alternately under three second wires and over one adjacent second wire among the plurality of second wires, and
   each second wire among the plurality of second wires passes alternately over three first wires and under one adjacent first wire among the plurality of first wires.

9. A method of conveying a continuous, air-permeable web, wherein the web is stretchable in a cross direction perpendicular to a conveyance direction of the web, said method comprising:
   placing the web on an endless belt which is rotatably supported by a plurality of rollers and has a plurality of suction portions penetrating the belt; and
   generating a suction force through the suction portions for sucking and holding the web on the belt while the web is being conveyed;
   wherein
   the belt further includes lifting portions each of which is provided between the suction portions adjacent in the cross direction and is raised from edge portions of the suction portions;
   the plurality of suction portions adjacent to each other across the lifting portions communicate with each other, when the web is sucked and held on the belt;
   the suction portions located at endmost portions in the cross direction of the belt communicate with the outside, when the web is sucked and held on the belt;

the web includes:
- a front waistline portion, a back waistline portion, and a crotch portion arranged between the front waistline portion and the back waistline portion in the cross direction;
- waist gathers which are disposed at a peripheral edge of the front waistline portion and a peripheral edge of the back waistline portion; and
- leg gathers which are disposed at both sides of the crotch portion; and the web is asymmetrical with respect to a center line, the center line bisecting a width of the web in the cross direction and extending in the conveyance direction.

\* \* \* \* \*